(12) United States Patent
Rubio et al.

(10) Patent No.: US 11,035,856 B1
(45) Date of Patent: Jun. 15, 2021

(54) RAPID ANALYSIS FOR CYANOBACTERIAL TOXINS

(71) Applicant: Abraxis, Inc., Warminster, PA (US)

(72) Inventors: Fernando Manuel Rubio, Doylestown, PA (US); Lisa Marie Kamp, Yardley, PA (US)

(73) Assignee: Abraxis, Inc., Warminster, PA (US)

( * ) Notice: Subject to any disclaimer, the term of this patent is extended or adjusted under 35 U.S.C. 154(b) by 0 days.

(21) Appl. No.: 16/838,123

(22) Filed: Apr. 2, 2020

Related U.S. Application Data

(60) Division of application No. 16/433,424, filed on Jun. 6, 2019, now Pat. No. 10,641,769, which is a continuation of application No. 13/941,524, filed on Jul. 14, 2013, now Pat. No. 10,338,067, which is a division of application No. 12/830,292, filed on Jul. 3, 2010, now Pat. No. 9,739,777, which is a continuation-in-part of application No. 12/204,911, filed on Sep. 5, 2008, now abandoned.

(60) Provisional application No. 60/970,432, filed on Sep. 6, 2007, provisional application No. 60/970,415, filed on Sep. 6, 2007.

(51) Int. Cl.
*G01N 33/569* (2006.01)

(52) U.S. Cl.
CPC .............................. *G01N 33/56911* (2013.01)

(58) Field of Classification Search
CPC ................................................ G01N 33/56911
See application file for complete search history.

*Primary Examiner* — Robert A Zeman
(74) *Attorney, Agent, or Firm* — Law Firm of Allan Fried; Allan H. Fried

(57) ABSTRACT

Method and compositions using transition metal salts and/or ammonium chloride to liberate toxins and other molecules from cyanobacteria, useful for assaying for total cyanobacterial toxins in lakes, reservoirs and other waters.

5 Claims, 2 Drawing Sheets

Lysis Time vs. Toxin Recovery Plot

- ■ 500 ppm CuSO4 + 0.001% Tween
- ▲ 250 ppm AgSO4 + 0.001% Tween
- ▼ Frozen and thaw 3X

*FIG. 1*

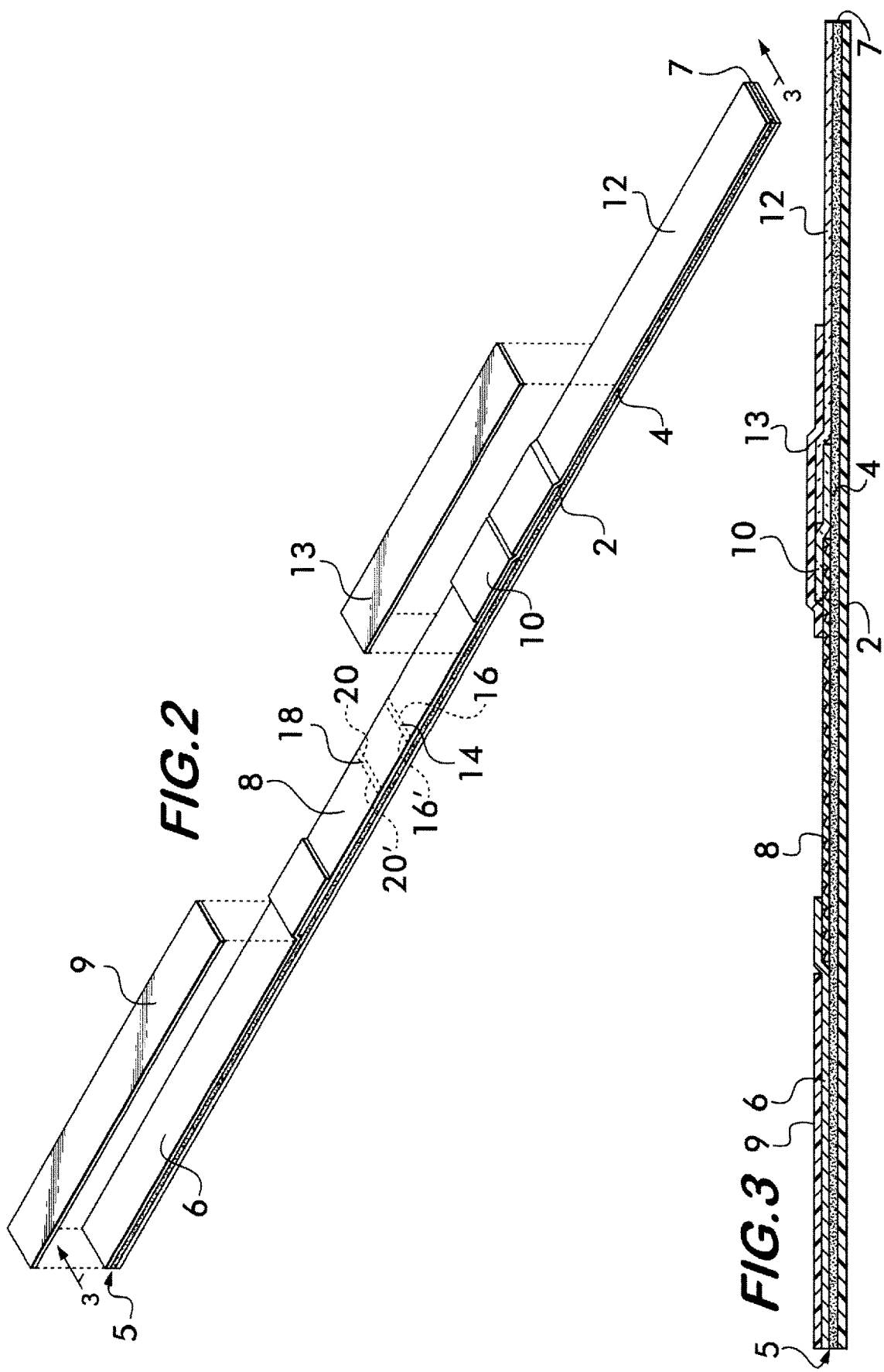

RAPID ANALYSIS FOR CYANOBACTERIAL TOXINS

CROSS REFERENCE TO RELATED APPLICATIONS

This application is a divisional application of US application Ser. No. 16/433,424, filed Jun. 6, 2019, which is a continuation application of U.S. application Ser. No. 13/941,524, filed Jul. 14, 2013, which is a divisional application of U.S. application Ser. No. 12/830,292 filed Jul. 3, 2010 (now granted as U.S. Pat. No. 9,739,777 on Aug. 22, 2017) which is a continuation-in-part application of U.S. application Ser. No. 12/204,911, filed Sep. 5, 2008 (now abandoned), which claims the benefit of U.S. provisional application Ser. No. 60/970,432, filed Sep. 6, 2007 and U.S. provisional application Ser. No. 60/970,415, filed Sep. 6, 2007. The entire disclosures of the foregoing divisional, continuation-in-part and provisional applications are incorporated herein by reference in their entireties.

FIELD OF THE INVENTION

This invention relates to methods for rapidly liberating cyanobacterial molecules, especially toxins, located within the bacteria, so as to make them accessible to detection and/or quantification.

BACKGROUND OF THE INVENTION

Some cyanobacteria can produce nerve, liver or derma toxins ("cyanotoxins"), making them dangerous to humans and animals. Because they occur in water that humans and animals either drink or come into contact with, it is necessary to test for their occurrence.

A problem with testing for cyanotoxins is that they occur not only in the water, but also inside cyanobacterial cells present in the water. Therefore, testing usually includes an initial step (freeze and thaw, boiling, microwaving, freeze-drying) that allows the toxins to be liberated from the bacteria into an aqueous medium, accessible to testing. This aspect of toxin testing has room for improvement, however, because faster means for efficient cyanobacterial extraction are needed. Although such improvement would be generally advantageous, it is of particular importance when the assays are done "in the field", rather than at a laboratory some distance from their source, and a rapid answer is necessary.

Cyanobacteria are a large and varied phylum of aquatic bacteria. They are also known as "blue-green algae", but are not related to any other algae, which are all eukaryotes. They occur in man-made reservoirs and naturally-occurring water sources, such as lakes, hot springs, rivers, marshes, streams, ponds and salt waters, as well as ocean and sea coastal areas. Depending on the species and environmental conditions, cyanobacteria may organize into large masses, referred to as "blooms", in which the bacteria may be filamentous, in sheets or even hollow balls.

There are numerous cyanobacterial species. A single cyanobacterial species can occur as either a toxic or non-toxic population, depending on environmental conditions or stress. Blooms that test non-toxic one day can turn toxic the next day.

One of the present inventions comprises the use of an appropriate metal salt, as specified herein, as a releasing agent to liberate cyanotoxins and other molecules rapidly from cyanobacteria. In a related invention, liberation of the cyanotoxins is achieved by exposing the cyanobacteria to such a metal salt and subsequently to ammonium chloride.

BRIEF SUMMARY OF THE INVENTION

In one general aspect, the invention is an improved process for determining the amount of cyanobacterial toxins in lakes, reservoirs and other waters, wherein the improvement is the use of a releasing agent, the releasing agent being a metallic sulfate and/or at least one salt of one of the following transition metals: Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg. In a closely related aspect of the invention, the improved process further comprises the addition of ammonium chloride to the sample of the water.

DETAILED DESCRIPTION OF THE DRAWINGS

FIG. 1. Graph showing effect of metallic sulfate addition on toxin recovery.
FIG. 2. Isometric view of a dipstick.
FIG. 3. Cross-sectional view of the dipstick shown in FIG. 2.

DETAILED DESCRIPTION OF THE INVENTION

In a first aspect, the invention is a method for extracting a molecule, especially a toxin, from cyanobacteria using a releasing agent. The releasing agent is a metallic sulfate (also referred to as a "metal sulfate") and/or at least one salt of one of the following transition metals: Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg. The cyanobacteria are suspended in liquid medium, preferably one in which the primary component is water, and treated with a releasing agent that liberates the toxin into the medium. It is possible that the releasing agent acts by increasing the permeability of the cyanobacterial membrane and/or lysing the cyanobacteria. Treatment involves either adding the releasing agent to the medium in which the cyanobacteria are suspended or adding the medium to a vessel containing the releasing agent. Addition to the medium can take place into the medium in which the cyanobacteria are already suspended or to the medium in which the cyanobacteria will be suspended. A test assay is then done for the presence and/or amount of the toxin in the liquid medium that has been treated with the releasing agent.

The term "metal salt", for purposes of the present inventions, is understood to mean a chemical compound comprising a metal atom—such as a silver, copper or gold atom—such that the compound will, to at least some extent, dissociate in water liberating the metal atom as a metal ion.

Examples of metal salts useful for the invention include, but are not limited to, silver, copper or gold salts. Accordingly, in one aspect of the invention, the releasing agent is one of the formula, $XSO_4$ or the formula, $X_2SO_4$, or the formula $X_3SO_4$ where X is a metal atom (which upon dissociation becomes a metal ion), such that: with $XSO_4$, X is copper or gold; with $X_2SO_4$, X is silver; and with $X_3SO_4$, X is gold. In the case of gold, it is generally necessary to disperse the gold sulfate, which tends to precipitate in aqueous solutions. Releasing agents can also be used in combination with detergents, such as Triton X-100 and Tween-20.

Also adding $NH_4Cl$ increases the reliability of the release because occasionally the metallic sulfate alone or the metal salt alone will not result in adequate release of the cyanotoxins. $NH_4Cl$ is preferably added subsequent to the addition of any other releasing agent (for example, a metallic sulfate or transition metal salt). Releasing agents are those agents that, compared to their absence, result in increased release of cyanobacterial molecules from cyanobacteria in aqueous solution.

It is hypothesized that the mechanism of release by a metallic sulfate or metal salt is due to bacterial lysis, but it may be due to increased permeability of the bacterial membrane. Generally it is preferred that the transition metal atom be present at a concentration of at least 0.005 mM. Examples of preferred concentrations of the releasing agents, when they are used to treat the cyanobacterial suspension, are in the range of 0.063 mM to 31.3 mM for copper and 0.032 mM to 16.0 mM for silver (which translates to 10 ppm to 5,000 ppm for copper sulfate ($CuSO_4$) and 10 ppm to 5,000 ppm for silver sulfate ($Ag_2SO_4$)), and more than 1000 ppm, preferably 2000 ppm, for $NH_4Cl$. Sufficient releasing agent must be used to release the toxin but not so much should be used so as to interfere with subsequent testing methods (either by leading to artificially high or low results). As the concentration of those releasing agents increases above 5,000 ppm, especially as it reaches 10,000 ppm and higher, the sample needs to be diluted, post-release, so that the releasing agent concentration is not greater than that resulting from using an undiluted 5000 ppm sample. The preferred times of cyanobacterial exposure to the releasing agent are in the range of 1 minute to 30 minutes. Two or more exposure times can be used to determine if the bacteria have been exposed to the releasing agent for a sufficient time to release all of the toxin. The medium into which the molecules are released may already contain molecules identical in structure to those released.

Toxins of particular interest are cyclic peptides, alkaloids, and lipopolysaccharides. Examples of cyclic peptides are microcystins and nodularins. Examples of alkaloids are anatoxin-a, anatoxin-a(S), aplysiatoxins, cylindrospermopsins, lyngbyatoxin-a, and saxitoxins.

Analytical test methods for toxin analysis are known in the art and include but are not limited to HPLC (High Pressure Liquid Chromatography) analysis, immunoassays which employ monoclonal or polyclonal antibodies specific for the toxin(s) of interest and protein phosphatase inhibition assays. The HPLC analysis can be followed by tandem mass spectrometry (the processes in combination referred to as LC/MS/MS) and further followed by reverse phase chromatography. Examples of immunoassays employing antibodies are enzyme-linked immunosorbent assays (ELISAs) and dipstick assays.

In an embodiment of particular interest, the toxin assay comprises the use of a "dipstick" where the dipstick comprises a stick or other solid object on whose surface toxin-specific binding agents (such as antibodies) or toxin-protein conjugates are immobilized. After toxin release from the cyanobacteria, the dipstick is immersed in the medium containing the toxins. The presence of toxin in the medium is determined by treating the dipstick in one or more steps, at least one comprising the use of toxin-specific antibodies, that result in an observable change (e.g., a color change) on the dipstick when the toxins are present in the medium. The extent of color change may be used as an indication of the amount of toxin bound. Calibration experiments in which known concentrations of toxin are used allow correlation of a color change with the concentration of the toxin in the medium tested. In the examples described below, if sufficient antibody is bound to the test line (as the antibody is a gold-labeled antibody), the gold is visible as a pink test line.

The dimensions of a typical dipstick are in the range of 50 mm to 110 mm length. The shape of the dipstick may vary, for example resembling that of a card, and allow for multiple toxins to be tested in the same card.

A preferred version of the dipstick is illustrated in FIGS. 2 and 3. The dipstick comprises a backing strip (2). A pressures-sensitive adhesive strip (4), both sides of which are capable of pressure-sensitive adhesion, is affixed to the backing strip (2). The other side of the adhesive strip (4) is affixed, sequentially in the direction from the distal end (5) to the proximal end (7) of the adhesive strip, to: the distal and predominant portion of an absorbent pad (6), a membrane (8), the proximal and predominant portion of a conjugate pad (10) and the proximal portion of a sample pad (12). The distal end (5) of the adhesive strip is part of the distal end of the dipstick. The proximal portion of the absorbent pad (6) overlaps and is in contact with the distal end of the membrane (8). The distal portion of the conjugate pad overlaps and is in contact with the proximal portion of the membrane (8). The distal portion of the sample pad (12) overlaps and is in contact with the proximal portion of the conjugate pad (10).

The width of the backing strip (2) and all other components of the dipstick is, for example, in the range of about 3 mm to about 5 mm. The length of the backing strip (2) and adhesive strip (4) is, for example, about 85 mm. The dimensions, in the distal-proximal dimension, of the component portions adhering directly to the adhesive strip are, for example: absorbent pad (6), about 29 mm; membrane (8), about 27 mm; conjugate pad (10), about 10 mm; and sample pad (12), about 33 mm. The total exceeds 85 mm because some of the components overlap. The dimensions, in the proximal-distal dimension, of components overlapping the membrane are: absorbent pad (6), about 4 mm; and conjugate pad (10), about 4 mm. In the proximal—distal direction there is about 7 mm of overlap between the conjugate pad (10) and the sample pad (12).

The backing strip (2) is made of plastic, the absorbent pad (6) is made of cotton lintner, the membrane (8) is made of nitrocellulose, the conjugate pad (10) is made of glass fiber, and the sample pad (12) is made of glass fiber tissue. Depending on the assay in which the dipstick is to be used, the conjugate pad (10) may contain, in dried form, monoclonal anti-microcystins antibodies labeled with colloidal gold particles.

The two surfaces in any overlap area are preferably in contact with each other. A proximal region flexible plastic cover strip (13), with sufficient adhesive to stick to the membrane (8), conjugate pad (10) and sample pad (12) is added to improve contact in overlap areas between those components. A distal region plastic cover sheet (9) with sufficient adhesive is added to the absorbent pad (6) to protect the pad.

Microcystin-BSA conjugate is coated to a test line area (14) (also referred to as the "capture line area") of the membrane (8). The boundaries of the test line area (14) are marked by two dashed lines (16, 16') and they are between about 0.5 mm to about 1.0 mm apart, which corresponds to the width of the area. Goat anti-mouse antibody (or protein A or protein G) is coated to a control line area (18) of the membrane (8). The boundaries of the control line area are marked by two dashed lines (20, 20') and they are between about 0.5 mm to about 1.0 mm apart, corresponding to the width of the area. The midline of the control line area (18; parallel to and halfway between the lines 20 and 20') is preferably about 7 mm from the proximal end of the absorbent pad (6). The distance from the midline of the control line area to the midline of the test line area is preferably about 5 mm. The length of both the control line and test line areas is that of the width of the dipstick, for example, in the range of about 3 mm to about 5 mm.

Related to the processes of the invention are kits for carrying out the processes. Such a kit will comprise a releasing agent. It may further comprise a means of detecting or facilitating the detection of a toxin. That means may optionally be one that will quantitate or facilitate the quantitation of the toxin. Examples of such means are toxin-specific antibodies, dipsticks that facilitate detection and/or quantitation of the toxin, and a means of treating the dipstick after the toxin has been allowed to bind to the dipstick to enable visualization or other confirmation that the toxin has bound to the dipstick. Such visualization means may, for example, comprise an antibody specific for the toxin to be assayed for, such antibody conjugated to a moiety that is directly observable (e.g., gold), or toxin that is conjugated to a means that indirectly allows visual detection (e.g., an enzyme, such as horse radish peroxidase, that will convert a substrate to a compound that has a characteristic color). The kits will preferably contain printed material (for example on paper or on a container for individual component(s) of the kit or for the entire kit) indicating the purpose of the kit is to be used in the detection of toxins and preferably indicating directions for using the kit.

In the use of the dipstick or other assays, it is not necessary that all of the released toxin react with the dipstick or other assay. The dipstick or assay may be calibrated (adding various known amounts of toxin to the medium and determining the results obtained with the dipstick or assay) so that the amount detected by the dipstick or assay can be used to calculate the total amount of toxin in the medium.

Two-letter abbreviations for atoms referred to herein are as follows (with their full names in parenthesis): Sc (scandium), Y (yttrium), La (lanthanum), Ti (titanium), Zr (zirconium), Hf (halfnium), V (vanadium), Nb (niobium), Ta (tantalum), Cr (chromium), Mo (molybdenum), W (tungsten), Mn (manganese), Tc (technitium), Re (rhenium), Fe (iron), Ru (ruthenium), Os (osmium), Co (cobalt), Rh (rhodium), Ir (iridium), Ni (nickel), Pd (palladium), Pt (platinum), Cu (copper), Ag (silver), Au (gold), Zn (zinc), Cd (cadmium), Hg (mercury).

Preferred metal salts for the present inventions are those that comprise an atom from the following group: Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg. The more preferred among that group of metal salts are those that comprise an atom from the following group: Sc, Y, La, Ti, Zr, Hf, V, Nb, Cr, Mo, W, Mn, Re, Fe, Ru, Os, Co, Rh, Ir, Ni, Pd, Pt, Cu, Ag, Au, Zn, Cd, and Hg. It is noted that all the metals on the lists are transition metals.

For copper salts, the following anions are preferred: the acetate, benzoate, bromide, chloride, chlorate, cyanide (but not for copper (II)), fluoride, formate, nitrate, perchlorate, and sulfate anions.

For silver salts, the following anions are preferred: the acetate, benzoate, chlorate, fluoride, formate, nitrate, perchlorate, sulfate, trifluoroacetate, and bromate.

For gold salts, the following anions are preferred: the acetate, benzoate, bromide, chloride, chlorate, fluoride, cyanide, formate, hydroxide, nitrate, perchlorate, and sulfate anions.

For chromium salts, the following anions are preferred: the acetate, benzoate, bromide, carbonate (for chromium (II)), chloride (but not for chromium (III)), chlorate, cyanide (but not for chromium (III)), fluoride, formate, iodide, nitrate, oxalate (for chromium (III)), perchlorate, and sulfate anions.

For manganese salts, the following anions are preferred: the acetate, benzoate, bromide, chloride, chlorate, cyanide, fluoride (but not for manganese(II)), formate, iodide, nitrate, perchlorate, and sulfate anions.

For iron salts, the following anions are preferred: the acetate, benzoate (but not for iron (III)), bromide, chloride, chlorate, citrate (for iron (III)), cyanide (but not for iron (II,III)), fluoride, formate, iodide, nitrate, oxalate (for iron (III)), perchlorate, sulfate, and tartrate (for iron (III)) anions.

For cobalt salts, the following anions are preferred: the acetate, benzoate, bromide, chloride, chlorate, cyanide (but not for cobalt (II)), fluoride, formate, iodide, nitrate, perchlorate, and sulfate anions.

For nickel salts, the following anions are preferred: the acetate, benzoate, bromide, chloride, chlorate, citrate (for nickel (II)), cyanide (but not for nickel(II)), fluoride, formate, iodide, nitrate, perchlorate, and sulfate anions.

For platinum salts, the following anions are preferred: the acetate, benzoate, bromide, chloride, chlorate, cyanide (but not for platinum (II)), fluoride, formate, iodide (but not for platinum (II)), nitrate, perchlorate, and sulfate anions.

For zinc salts, the following anions are preferred: the acetate, benzoate, bromide, chloride, chlorate, fluoride, formate, iodide, nitrate, perchlorate, and sulfate anions.

For mercury salts, the following anions are preferred: the acetate, benzoate (but not for mercury (I)), bromide (but not for mercury (I)), chloride (but not for mercury (I)), chlorate, cyanide (but not for mercury (I)), fluoride, formate, iodide (but not for mercury (I,II)), nitrate, perchlorate, and sulfate anions.

For scandium, the following anions are preferred: the chloride and oxide (for scandium (III)) anions.

For yttrium, the following anions are preferred: the chloride (for yttrium (III)) and iodide (for yttrium (III)) anions.

For lanthanum, the following anions are preferred: the chloride heptahydrate (for lanthanum (III)) and nitrate hydrate (for lanthanum III)) anions.

For titanium, the following anions are preferred: the chloride and fluoride (for titanium (III)) anions.

For zirconium, the following anions are preferred: the hydroxide (for zirconium (IV)) and iodide (for zirconium (IV)) anions.

For hafnium, the following anion is preferred: the dichloride oxide anion.

For vanadium, the following anions are preferred: the chloride (for vanadium (II)) and iodide (for vanadium (III)) anions.

For niobium, the following anion is preferred: the bromide (for niobium(V)) anion.

For molybdenum, the following anion is preferred: the trioxide anion.

For tungsten, the following anion is preferred: the sodium tungsten oxide dihydrate anion.

For rhenium, the following anion is preferred: the chloride (for rhenium (III)) anion.

For ruthenium, the following anion is preferred: the chloride (for ruthenium (III)) anion.

For osmium, the following anion is preferred: the tetroxide anion.

For rhodium, the following anion is preferred: the acetate (for rhodium (II)) anion.

For iridium, the following anion is preferred: the chloride (for iridium (III)) anion.

For palladium, the following anions are preferred: the chloride (for palladium (II)) and nitrate (for palladium (II)) anion.

For cadmium, the following anions are preferred: the chloride and iodide anions.

The solubility of a transition metal salt in aqueous solution is a limiting factor that can prevent its effectiveness. Therefore the invention is primarily directed at sufficiently soluble salts that increase cyanobacterial toxin recovery. The desired increased recovery is defined as a "corrected cyanotoxin recovery of at least 15%" (See Paragraph 4 below).

Accordingly, the invention in many (but not all) aspects can be summarized by the following numbered paragraphs 1 through 42:

1. A method of testing for a cyanobacterial toxin in a suspension comprising cyanobacteria suspended in an aqueous medium, wherein said method comprises adding a releasing agent to the suspension so as to release toxins from the bacteria into the medium, and subsequently performing a test assay for the toxin, wherein the releasing agent is a metal salt that comprises an atom selected from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg.
2. A method of paragraph 1 wherein the metal salt comprises a sulfate anion
3. A method of Paragraph 1 wherein the releasing agent is a metal salt that comprises a metal atom selected from the group consisting of a silver atom, copper atom, and a gold atom.
4. A method of paragraphs 1, 2 or 3 in which the corrected cyanobacterial toxin recovery obtained by adding the releasing agent to a first aliquot of the suspension is at least 15 percent of the corrected cyanobacterial toxin recovery obtained by freezing and thawing of a second aliquot of said suspension in the absence of the releasing agent, where each corrected recovery is the recovery obtained less a background recovery equal to the cyanobacterial toxin recovery obtained with a third aliquot of the suspension, said third aliquot being one to which the releasing agent has not been added and which has not been frozen or thawed. It is understood that the recovery for all three aliquots is to be expressed as recovery per unit volume of suspension. To illustrate with hypothetical data, if the recovery with the third aliquot is 2.0 ppb and the recovery with the first aliquot is 5.0 ppb, then the corrected recovery with the first aliquot is 3.0 ppb. Similarly if the recovery with the second aliquot is 12.0 ppb, then the corrected recovery with the second aliquot is 10.0 ppb. In such hypothetical, the corrected recovery for the first aliquot (that obtained by adding the releasing agent) is 30 percent of the corrected recovery with the second aliquot (that obtained by freezing and thawing). For this calculation, it is understood that, with the exception that one aliquot is exposed to the releasing agent, one to freezing and thawing, and one to neither a releasing agent nor to freezing or thawing, the three aliquots are subjected to the same processing and analysis.
5. A method of Paragraphs 1, 2, 3 or 4, wherein the metal salt comprises a silver atom.
6. A method of Paragraph 5 wherein the metal salt is selected from the group consisting of silver acetate, silver benzoate, silver chlorate, silver fluoride, silver formate, silver nitrate, silver perchlorate, silver sulfate, silver trifluoroacetate, and silver bromate.
7. A method of Paragraph 6 wherein the metal salt is silver sulfate.
8. A method of Paragraph 1, 2, 3 or 4 wherein the metal salt comprises a copper atom.
9. A method of Paragraph 8 wherein the metal salt is a copper salt selected from the group consisting of copper acetate, copper benzoate, copper bromide, copper chloride, copper chlorate, copper cyanide (but not for copper (II)), copper fluoride, copper formate, copper nitrate, copper perchlorate, and copper sulfate.
10. A method of Paragraph 9 wherein the copper salt is copper sulfate.
11. A method of paragraph 1, 2, 3 or 4 wherein the metal salt comprises a gold atom.
12. A method of Paragraph 11 wherein the gold salt is selected from the group consisting of gold acetate, gold benzoate, gold bromide, gold chloride, gold chlorate, gold fluoride, gold cyanide, gold formate, gold hydroxide, gold nitrate, gold perchlorate, and gold sulfate.
13. A method of Paragraph 2 wherein the releasing agent is a metal sulfate of the formula $XSO_4$, $X_2SO_4$, or $X_3SO_4$ where X is an atom selected from the group consisting of copper, silver or gold.
14. A method of any one of Paragraphs 1 through 13 wherein a detergent is also present in the suspension in addition to the releasing agent (said detergent preferably selected from the group consisting of Triton X-100 and Tween-20).
15. A method of any one of Paragraphs 1 through 14 wherein the toxin is selected from the group consisting of microcystins, nodularins, anatoxin-a, anatoxin-a(S), aplysiatoxins, cylindrospermopsins, lyngbyatoxin-a, and saxitoxins.
16. A method of any one of Paragraphs 1 through 15 wherein ammonium chloride is added to the suspension subsequent to the addition of the metal salt but prior to performing the test assay.
17. A method of any one of Paragraphs 1 through 16 wherein the test method is selected from the group consisting of HPLC, an immunoassay utilizing antibodies, and protein phosphatase inhibition assays.
18. A method of Paragraph 17 wherein the test method is selected from the group consisting of HPLC and an immunoassay utilizing antibodies.
19. A method of any one of paragraphs 1, 2, 3, 4, or 5 provided that the metal salt is not silver sulfate.
20. A method of Paragraph 19 wherein the toxin is selected from the group consisting of microcystins, nodularins, anatoxin-a, anatoxin-a(S), aplysiatoxins, cylindrospermopsins, lyngbyatoxin-a, and saxitoxins.
21. A method of testing for a cyanobacterial toxin in a suspension comprising cyanobacteria suspended in an aqueous medium, wherein said method comprises (1) adding a releasing agent other than ammonium chloride and (2) ammonium chloride (preferably subsequent to the addition of the releasing agent other than ammonium chloride) to the suspension so as to release toxins from the bacteria into the medium, and subsequently performing a test assay for the toxin.
22. A kit comprising a releasing agent that is a metal salt that comprises an atom selected from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg, and further comprising an antibody specific for a toxin.
23. A kit of paragraph 22 wherein the metal salt comprises a sulfate anion.

24. A kit of Paragraph 23 wherein the metal salt is of the formula, $XSO_4$ or $X_2SO_4$, or $X_3SO_4$ where X is a metal atom selected from the group consisting of copper, silver, and gold.
25. A kit of Paragraph 24 wherein the metal salt comprises a silver atom.
26. A kit of Paragraph 25 wherein the metal salt is selected from the group consisting of silver acetate, silver benzoate, silver chlorate, silver fluoride, silver formate, silver nitrate, silver perchlorate, silver sulfate, silver trifluoroacetate, and silver bromate.
27. A kit of Paragraph 26 wherein the metal salt is silver sulfate.
28. A kit of Paragraph 24 wherein the metal comprises a copper atom.
29. A kit of Paragraph 28 wherein the metal salt is selected from the group consisting of copper acetate, copper benzoate, copper bromide, copper chloride, copper chlorate, copper cyanide (but not for copper (II)), copper fluoride, copper formate, copper nitrate, copper perchlorate, and copper sulfate.
30. A kit of Paragraph 29 wherein the metal salt is copper sulfate.
31. A kit of Paragraph 27 wherein the metal salt comprises a gold atom.
32. A kit of Paragraph 31 wherein the metal salt is selected from the group consisting of gold acetate, gold benzoate, gold bromide, gold chloride, gold chlorate, gold fluoride, gold cyanide, gold formate, gold hydroxide, gold nitrate, gold perchlorate, and gold sulfate.
33. A kit of any one of Paragraphs 22 through 32 which further comprises a detergent (said detergent preferably selected from the group consisting of Triton X-100 and Tween-20).
34. A kit of any one of Paragraphs 22 though 33 wherein the toxin is selected from the group consisting of microcystins, nodularins, anatoxin-a, anatoxin-a(S), aplysiatoxins, cylindrospermopsins, lyngbyatoxin-a, and saxitoxins.
35. A kit of any one of Paragraphs 22 through 34 further comprising ammonium chloride.
36. A kit of paragraphs 22, 23, 24, 25, 26, 33 or 35 provided that the metal salt is not silver sulfate.
37. A kit of paragraph 36 wherein the toxin is selected from the group consisting of microcystins, nodularins, anatoxin-a, anatoxin-a(S), aplysiatoxins, cylindrospermopsins, lyngbyatoxin-a, and saxitoxins.
38. A kit for testing for a cyanobacterial toxin in a suspension, said kit comprising (1) a releasing agent other than ammonium chloride; (2) ammonium chloride; and (3) an antibody specific for a toxin.
39. Any of the methods or kits of the preceding paragraphs 1 through 38 where the toxin is selected from the group consisting of a microcystin and a nodularin.
40. Any of the methods or kits of the preceding paragraphs 1 through 38 where the toxin is a microcystin.
41. Any of the kits of the preceding paragraphs 22 through 40 wherein the kit comprises instructions for using the kit to measure the toxin that reacts with the antibody specific for the toxin.
42. Any of the kits of the preceding paragraphs 22 through 41 wherein the components of the kit set forth in said paragraph are all in the same package (e.g. a box).

Example 1

Use of Copper Sulfate or Silver Sulfate—ELISA as the Test Assay

Aliquots of lake water were obtained from a lake in Pinellas County, Fla., and used for the data in Tables 1 through 6. A volume of 100 ul was used in the assay. Each sample, unless otherwise indicated in the Tables, was prepared as follows: to 980 uL of sample, added 10 uL of a copper sulfate solution and 10 uL of 0.1% Tween-20 solution (1:100 dilution in the sample, so that if the copper sulfate solution contained 50,000 ppm copper sulfate, the resulting concentration was then 500 ppm copper sulfate, 0.001% Tween-20) (or no such reagent, for purposes of a control). (The 0.1% Tween-20 solution was prepared by diluting a 100% Tween-20 solution by a factor of 1:999 in deioinized water). The total of the combined volumes of sample and reagents was therefore 1000 uL and the combination was referred to as the releasing reaction mixture. As indicated in the Tables, in some cases, the final concentration of Tween was varied, or Triton was used instead of Tween.

Aliquots of lake water were also obtained from Lake Wauberg, Fla. They were used for the data in Table 7. The sample was prepared as follows: to 940 uL of sample, added 50 uL of a 5,000 ppm silver sulfate solution, and 10 uL of 0.1% Tween-20 solution (1:20 dilution and 1:100 dilution in the sample, respectively, so that the resulting concentration was 250 ppm silver sulfate, 0.001% Tween-20). A volume of 100 ul of the post-release sample was used in the assay.

At the end of the reaction time (10 minutes for both the Pinella County and Lake Wauberg samples unless otherwise specified), a volume of 0.1 ml (100 ul) of the post-release sample was tested using an Abraxis, LLC Microcystins-DM ELISA Microtiter plate assay (Part Number 522015). The assay is a direct competitive ELISA. The volume of either microcystin standard solution (see below) or post-release sample to be tested (0.1 ml), 0.05 mL HRP (horse radish peroxidase)-labeled microcystin, and 0.05 mL of the anti-microcystin antibody were added to the wells of an ELISA plate coated with goat anti-mouse antibodies. Toxin in the post-release sample was allowed to compete with the enzyme-labeled microcystin for the antibody binding sites for a period of 90 minutes at 20-25° C. Unbound labeled microcystin was washed away using PBS (phosphate-buffered saline)-Tween wash buffer. The enzymes bound to the plates were allowed to react with TMB (tetramethylbenzidine) in buffer (the TMB in buffer is obtained from BioFx (Owens Mills, Md.)) for 20 minutes and 0.1 mL of diluted sulfuric acid was then added to stop the reaction. Substrate-reaction buffers are also available from other companies. The color intensity was determined at 450 nm using a Molecular Devices VMax Plate Reader. The extent to which color was decreased relative to controls, microcystins standard solutions that consisted of Microcystin-LR at various concentrations in 0.1% ProClin (purchased from Supelco) in water, was a measure of the amount of microcystins in the post-release sample and therefore the sample of lake water.

The microcystin-specific antibodies used in the ELISA were monoclonal antibodies obtained from a hybridoma cell line (AD4G2; Ref: Michael G. Weller Analytical Science, 2001, Vol. 17 pages 1445-1448) obtained from IPC/TMC of Neuwilen, Switzerland. Similar-functioning antibodies are also obtainable from Envirologix, Portland, Me., and Strategic Diagnostics, Inc., Newark, Del.

Related Results are in the Following Tables:

TABLE 1

| Reaction volume Contained lake water sample #3 plus: | Microcystin concentration determined by the assay (ppb) | % Recovery |
|---|---|---|
| Nothing added | 3.06 | 42 |
| Nothing added but frozen & thawed 3X | 7.32 (Defines 100%) | 100 |
| 5% Tween | 2.92 | 40 |
| 2% Tween | 2.59 | 35 |
| 1% Tween | 2.67 | 37 |
| 5% Triton | 2.92 | 40 |
| 2% Triton | 2.52 | 34 |
| 1% Triton | 2.55 | 35 |

TABLE 2

| Reaction volume Contained lake water sample #4 plus: | Microcystin concentration determined by the assay (ppb) | % Recovery |
|---|---|---|
| Nothing added | 1.59 | 22 |
| Nothing added but frozen & thawed 3X | 7.32 | 100 |
| 10 ppm CuSO4 | 2.40 | 33 |
| 100 ppm CuSO4 | 2.31 | 32 |
| 1000 ppm CuSO4 | 7.25 | 99 |

TABLE 3

| Reaction volume Contained lake water sample #5 plus: | Microcystin concentration determined by the assay (ppb) | % Recovery |
|---|---|---|
| Nothing added | 1.17 | 20 |
| Nothing added but frozen & thawed 3X | 5.85 | 100 |
| Nothing added but frozen & thawed 1X | 5.15 | 88 |
| Nothing added but heated for 2 min at 63° C. | 5.40 | 92 |
| 1000 ppm CuSO4 | 5.17 | 88 |

TABLE 4

| Reaction volume Contained lake water sample #6 plus: | Microcystin concentration determined by the assay (ppb) | % Recovery |
|---|---|---|
| Nothing added | 0.75 | 16 |
| Nothing added but frozen & thawed 3X | 4.84 | 100 |
| 1000 ppm CuSO4 for 10 min | 4.28 | 88 |
| 1000 ppm CuSO4 for 20 min | 4.96 | 102 |
| 1000 ppm CuSO4 for 30 min | 5.64 | 116 |

TABLE 5

| Reaction volume Contained lake water sample #7 plus: | Microcystin concentration determined by the assay (ppb) | % Recovery |
|---|---|---|
| Nothing added | 0.77 | 18 |
| Nothing added but frozen and thawed 3X | 4.31 | 100 |
| 5000 ppm CuSO4 | 4.79 | 111 |
| 2% lysozyme/EDTA | 0.66 | 15 |
| 1000 ppm CuSO4, 2% Tween | 6.62 | 154 |
| 1000 ppm CuSO4, 2% Triton | 4.51 | 105 |

TABLE 6

| Reaction volume Contained lake water sample #8 plus: | Microcystin concentration determined by the assay (ppb) | % Recovery |
|---|---|---|
| Nothing added | 0.19 | 4 |
| Nothing added but frozen and thawed 3X | 4.42 | 100 |
| 100 ppm Al$_2$(SO4)$_3$ | 0.45 | 10 |
| 1000 pm CuSO4, 0.01% Tween | 5.96 | 135 |
| 1000 pm CuSO4, 0.01% Triton | 7.87 | 178 |
| 0.1% SDS | 14.13 | 319 |
| 1000 ppm CuSO4, 0.1 SDS |  | >400 |

Percent recovery (% Recovery) values in excess of 135 generally reflect interference.

TABLE 7

| Reaction volume Contained lake water sample #10 plus: | Microcystin concentration determined by the assay (ppb) | % Recovery |
|---|---|---|
| Nothing added but frozen and thawed 3X | 2.84 | 100 |
| 500 ppm CuSO4, 0.001% Tween, 1 min | 1.76 | 62 |
| 250 ppm Ag2SO4, 0.001% Tween, 1 min | 2.35 | 83 |
| 500 ppm CuSO4, 0.001% Tween, 2 min | 1.94 | 68 |
| 250 ppm Ag2SO4, 0.001% Tween, 2 min | 2.57 | 91 |
| 500 ppm CuSO4, 0.001% Tween, 5 min | 2.31 | 81 |
| 250 ppm Ag2SO4, 0.001% Tween, 5 min | 2.7 | 95 |
| 500 ppm CuSO4, 0.001% Tween, 30 min | 2.78 | 98 |
| 250 ppm Ag2SO4, 0.001% Tween, 30 min | 2.86 | 101 |

The results of Table 7 are shown graphically in FIG. 1.

Example 2

Use of Copper Sulfate or Silver Sulfate—Immunoassay-Based Dipstick Procedure as the Test Assay A dipstick version of the invention is performed by, for example, using aliquots of lake water, an example of a "recreational water". A volume of 200 ul is used in the assay. The sample is prepared as follows: to 980 uL of sample, added 10 uL of a 50,000 ppm copper sulfate solution and 10 uL of 0.1% Tween-20 solution (1:100 dilution in the sample, so that the concentration is 500 ppm copper sulfate, 0.001%

Tween-20). The total of the combined volumes is therefore 1000 uL and the combination is referred to as the post-release reaction mixture.

Alternatively, as an example, an aliquot of lake water is prepared as follows: to 50 uL of a 5,000 ppm silver sulfate, and 10 uL of 0.1% Tween-20 solution were added to 940 uL (1:20 and 1:100 dilutions respectively in the sample, resulting concentration is 250 ppm silver sulfate, 0.001% Tween-20). At the end of the reaction time with the releasing agent (10 minutes, for example), a volume of 200 ul of the foregoing 1000 uL post-release sample is used in a dipstick assay. A schematic example of such a dipstick is shown in FIGS. 2 and 3 and is described above.

The dipstick assay is optionally an indirect competitive immunoassay. Monoclonal anti-microcystins antibodies labeled with colloidal gold particles are deposited in the conjugate pad (10) and dried. The volume of post-release sample to be tested is 0.2 ml and is brought in contact with the sample pad (12). The post-release sample will distribute itself through the sample pad (12) into the conjugate pad (10) by migrating towards the distal end (5) of the dipstick. Accordingly, microcystin molecules in the post-release sample are presented with the opportunity to bind with the gold labeled anti-microcystins antibodies from the conjugate pad (10). Gold-labeled antibodies also migrate via the membrane (8) to the test line area (14) and, if not already reacted with microcystins from the post-release sample, will bind to the microcystin—BSA conjugate in the test area line (14) so as to create a visible (pink) line. Excess gold-labeled antibodies that migrate towards the distal end (5) of the dipstick, past the test line area (14), will be available to be bound by the goat anti-mouse antibodies on the control line area (18) so as to create a visible (pink) line covering the control line area. The relative proportions of microcystin-BSA conjugate in the test line area (14) and goat anti-mouse antibody in the control line area (18) are, when the dipstick is constructed, adjusted so that the intensity of the color (pink) of the two line areas will be the same when the assay is performed under conditions where no microcystins are present in the post-release sample. After a period of 10-15 minutes (at 10-30° C.) from the time the dipstick is contacted with the post-release sample, the color of the dipstick's test line area (14) is determined visually and compared to the color of the dipstick's control line area (18). The extent to which the test line color is decreased is a measure of the amount of microcystins in the reaction sample and therefore the sample of lake water.

The microcystin-specific antibodies used in the dipstick assay are the same as those used for Example 1.

The reaction can be calibrated as to a color change using known amounts of Microcystin-LR.

The system was tested by using the indirect competitive immunoassay dipstick assay described in this Example with samples spiked with increasing amounts of microcystins (0, 5, 10, 20 ng/ml and also 0, 10, 20, 50 ng/ml (ppb)). The results showed that, using the dipstick criteria in Table 8, microcystins can be qualitatively screened, obtaining proper discrimination according to the criteria in Table 8.

TABLE 8

(Dipstick interpretation criteria)

| Control line | Test line | Interpretation | Dipstick Type |
| --- | --- | --- | --- |
| None visible | None visible | Invalid | |
| Visible | Not visible | Toxin > 10 ng/ml | Recreational Water (10 ppb sensitivity) |

TABLE 8-continued (Dipstick interpretation criteria)

| Control line | Test line | Interpretation | Dipstick Type |
| --- | --- | --- | --- |
| Visible | Not visible | Toxin > 5 ng/ml | Source Drinking Water (1 ppb sensitivity) |
| Visible | Visible - moderate intensity | Toxin between 0 and 10 ng/ml | Recreational Water |
| Visible | Visible - moderate intensity | Toxin between 0 and 5 ng/ml | Source Drinking Water |

Example 3

Use of Silver Sulfate—Immunoassay-Based Dipstick Procedure as the Test Assay

The dipstick assay with gold conjugate on the conjugate pad is described in Example 2 using copper sulfate. Such an assay can also be used with silver sulfate or other metal salts. The dipstick assay with the gold conjugate in the microcentrifuge tube is described in this example, Example 3, using silver sulfate. Such an assay can also be used with copper sulfate or other metal salts.

A dipstick version of the invention can also be performed by, for example, using aliquots of lake water and the dipstick shown in FIGS. 2 and 3, but without anti-microcystins antibodies (either unlabeled or labeled, such as with colloidal gold particles) in the conjugate pad (10). This approach is preferred to that described in Example 2.

The sample is prepared as follows: to 900 uL of sample, added 100 uL of a silver sulfate/Tween-20 solution (5,000 ppm silver sulfate plus 0.01% Tween-20 solution such that the resulting concentration in samples is 500 ppm silver sulfate, 0.001% Tween-20). This can also be achieved by drying (lyophilizing) the silver sulfate and Tween-20 reagents onto the inside of a glass vial. When using dry reagents (dried inside a glass vial via lyophilization), one can add 1000 ul of sample to the dried reagents in the vial. At the end of the reaction time with the releasing agent (10 minutes, for example), a volume of 200 ul of the foregoing 1000 uL post-release sample is used in the dipstick assay.

The assay is an indirect competitive immunoassay. Monoclonal anti-microcystins antibodies labeled with gold particles are deposited into a conical microcentrifuge test tube then dried. A 200 uL portion of the post-release sample is added to the test tube which is then shaken for an incubation period of 30 seconds when a recreational water is tested. (If a source of drinking water is tested, the sample undergoes an additional 20 minute incubation in the test tube). The microcystins in the reaction mixture are allowed to bind with the gold labeled anti-microcystins antibody during that incubation period. The proximal portion of the sample pad (12) is then immersed in the sample in the test tube for a period of 10 minutes at 10-30° C. The sample will then distribute itself into the sample pad and migrate towards the absorbent pad (6). Accordingly, the gold-labeled anti-microcystin antibodies, if not already bound to microcystins from the post-release sample, will have the opportunity to bind to the microcystin-BSA conjugate in the test line area (14) and, if not bound to those conjugates, will be bound to the goat anti-mouse antibody on the control line area (18). The dipstick is removed from the test tube and 5 minutes are allowed for the color to continue developing. The color (pink) of the dipstick's test line area (14) is determined visually and compared to the color of the dipstick's control line area (18). The extent to which the test line color is decreased is a measure of the amount of microcystins in the reaction sample and therefore the sample of lake water.

The microcystin-specific antibodies used in the dipstick assay are the same as those used for Example 1 ELISA.

Dipstick interpretation criteria are listed in Table 8.

The system was evaluated by using the assay described in this Example with the water samples spiked with increasing amounts of microcystins (0, 0.5, 1.0, 2.5, and 10 ng/ml (ppb)). The results showed that, using the dipstick criteria in Table 8, microcystins can be qualitatively screened, obtaining proper discrimination according to the criteria in Table 8.

Example 4

Use of Ammonium Chloride and Silver Sulfate—ELISA as the Test Assay

Aliquots of lake water were obtained from lakes in Delaware and used for the data in Table 9. Each sample was prepared as follows: 1 mL of sample was added to a vial containing dried reagents (100 uL of 5 mg/mL $Ag_2 SO_4$/0.02% Tween-20 solution). The vial was capped and shaken for 2 minutes then allowed to sit for 8 minutes. The resulting concentration was then 500 ppm silver sulfate, 0.002% Tween-20. A 1 cm×0.5 cm portion of Whatman filter paper No. 1 which had been soaked in a 300 mg/mL ammonium chloride solution and then dried was then added to the vial. The vial was shaken for 2 minutes and then allowed to sit for 8 minutes. The combination of these reagents, silver sulfate, Tween-20 and ammonium chloride, are referred to as the "releasing reaction mixture". Reagents-treated samples are referred to as "post-release samples".

At the end of the reaction time (20 minutes unless otherwise specified), the post-release samples were tested along with untreated portions of the same samples of lake water which had been frozen then thawed three times (the most commonly used procedure for cell lysis in the prior art). The samples were tested using an Abraxis, LLC Microcystins-DM ELISA Microtiter plate assay (Part Number 522015). The assay is a direct competitive ELISA. The volume of either microcystin standard or post-release sample to be tested (0.1 ml) was added to a well of an ELISA microtiter plate, which well was coated with goat anti-mouse antibodies. Then 0.05 mL HRP (horse radish peroxidase)-labeled microcystin, and 0.05 mL of the anti-microcystin antibody were added to the well. Toxin in the post-release sample was allowed to compete with the enzyme-labeled microcystin for the antibody binding sites for a period of 90 minutes at 20-25° C. Unbound labeled microcystin was then washed away using PBS (phosphate-buffered saline)-Tween wash buffer (10 mM phosphate saline, pH 7.4 with 0.02% Tween). The enzymes bound to the plates were allowed to react with TMB (tetramethylbenzidine) in buffer as a substrate (the TMB in buffer was obtained from BioFx, Owens Mills, Md.) for 20 minutes and 0.1 mL of diluted sulfuric acid was then added to stop the reaction. Substrate-reaction buffers are also available from other companies. The intensity of the color was determined at 450 nm using a Molecular Devices VMax Plate Reader. The extent to which color was decreased was a measure of the amount of microcystins in the post-release sample and therefore the sample of lake water. The reaction was calibrated as to a color change using control containing known amounts of Microcystin-LR.

The microcystin-specific antibodies used in the ELISA were monoclonal antibodies obtained from a hybridoma cell line (AD4G2; Ref: Michael G. Weller Analytical Science, 2001, Vol. 17 pages 1445-1448) obtained from IPC/TMC of Neuwilen, Switzerland. Similar-functioning antibodies are also obtainable from Envirologix, Portland, Me., and Strategic Diagnostics, Inc., Newark, Del. The results are shown in Table 9 and demonstrate that the lysis procedure provides for release of microcystins that is as effective as that obtained with the more time-consuming procedure of freezing and thawing 3 times.

TABLE 9

| Sample ID | Microcystin concentration determined by the ELISA after freeze and thaw (3X) (ppb) | Microcystin concentration determined by the ELISA after Reagent Lysis (ppb) | % Recovery |
|---|---|---|---|
| SLD 9/13/07 Cove #2 Surface | 1.27 | 1.40 | 110 |
| SLD 9/13/07 Spillway #4 Surface | 1.95 | 2.27 | 116 |
| SLD 9/13/07 Cove offshore #6 Surface | 4.25 | 4.92 | 116 |
| SLD 9/13/07 Cove offshore #7 Surface | 23.28 | 21.22 | 91 |

Alternatively, the releasing agents can also be used in a liquid solution form. Samples are prepared as follows: 1.0 mL of sample is added to a glass vial, followed by 0.1 mL of the first releasing agent solution, 5 mg/mL silver sulfate/0.01% Tween-20 in deionized water. The vial is then capped and the sample shaken for 2 minutes then allowed to sit for 8 minutes. The resulting concentration is 455 ppm silver sulfate, 0.001% Tween-20. A 0.01 mL aliquot of 200 mg/mL ammonium chloride is then added. The vial is capped and shaken for 2 minutes, then allowed to sit for 8 minutes. The sample is then ready for analysis. When quantitative results are to be determined from samples prepared with liquid solutions of the releasing agents, results will need to be multiplied by a factor of 1.11 to account for the dilution of the sample with the releasing agents. (All results that are shown in the Tables herein and which resulted from the use of liquid reagents rather than liquid reagents dried into vials or onto filter paper have been corrected for the liquid reagent dilution and do not require additional correction factors.)

Example 5

Use of Ammonium Chloride—Immunoassay-Based Dipstick Procedure as the Test Assay

A dipstick version is performed as described in Example 3 on post-release samples which have been lysed as in Example 4. It is also possible to use the dipstick assay described in Example 2.

The microcystin-specific antibodies used in the dipstick assay are the same as those used in Example 1.

The dipstick reaction is calibrated as to a color change using known amounts of Microcystin LR.

Dipstick interpretation criteria are listed in Table 8.

The system was evaluated by using the dipstick assay referred to in Example 3 with the water samples spiked with increasing amounts of microcystins (0, 0.5, 1.0, 2.5, and 10 ng/ml (ppb)). The results showed that, using the dipstick criteria in Table 8, microcystins can be qualitatively screened obtaining proper discrimination.

Example 6

Use of Ammonium Chloride and Silver Sulfate—LC/MS/MS as the Test Assay

A comparison was made, using LC/MS/MS to analyze samples, of the cell lysis procedure described in Example 4 to the conventional, prior art freeze and thaw method. The volume of post-release sample tested (0.1 ml) was added to and analyzed with an HPLC instrument (using a Shimadzu Prominence LC instrument) and the microcystin fraction was further resolved into various microcystin congener classes by tandem mass spectrometry (using an Applied Biosystems API 5000 Triple Quadrupole Mass Spectrometer) to separate the microcystins. Microcystin congener classes obtained by that process were further resolved by reverse-phase chromatography to identify specific congeners, measured in MRM mode, and quantitated by standard addition. The results are shown in Table 10 where MCLF, MCLR, MCLY, MCRR and MCYR refer to specific congeners of microcystins. It can be seen that the results obtained with post-release samples obtained as in Example 4 were similar to that obtained by freezing and thawing.

TABLE 10

Cyanotoxin Concentrations (g/L) by LC/MS/MS.

| Site Location/Lysis method | MCLF | MCLR | MCLY | MCRR | MCYR |
|---|---|---|---|---|---|
| Cove #2 | | | | | |
| Example 4 | >0.010 | 1.8 | >0.010 | 1.7 | >0.010 |
| Freeze/Thaw | >0.010 | 1.3 | >0.010 | 1.2 | >0.010 |
| Cove Offshore #6 | | | | | |
| Example 4 | >0.010 | 3.2 | >0.010 | 0.72 | >0.010 |
| Freeze/Thaw | >0.010 | 2.5 | >0.010 | 0.60 | >0.010 |
| Cove Offshore #7 | | | | | |
| Example 4 | 0.10 | 3.9 | 0.53 | 6.1 | 0.093 |
| Freeze/Thaw | 0.079 | 4.7 | 0.40 | 3.8 | 0.087 |
| Spillway #4 | | | | | |
| Example 4 | 0.34 | 21 | >0.010 | 15 | 0.68 |
| Freeze/Thaw | 0.25 | 26 | >0.010 | 16 | 0.58 |

Example 7

Use of Silver Acetate or Silver Nitrate—ELISA as the Test Assay

Aliquots of lake water were obtained from a lake in Florida and used for the data in Tables 11 through 15. Each sample was prepared according to the following releasing protocol: 1 mL of lake sample was added to a vial, followed by 10 ul of a 5 mg/mL silver acetate solution. The vial was capped and shaken for 2 minutes then allowed to sit for 8 minutes for a total incubation time of 10 minutes. The resulting concentration was then 49.5 ppm silver salt.

At the end of the 10 minute reaction time, which corresponded to the end of the releasing protocol, the resulting sample, referred to as the "silver acetate sample", was subjected to ELISA analysis.

For the ELISA analysis, the silver acetate sample was tested using an Abraxis, LLC Microcystins-ADDA ELISA Microtiter plate assay (Part Number 520011). The assay is an indirect competitive ELISA. The volume of either microcystin standard or post-release sample to be tested (0.05 ml) was added to a well of an ELISA microtiter plate, which well was coated with a microcystin analog, ADDA-hemaglutaryl, prepared by the procedure set forth in W. J. Fischer et al., Congener-independent Immunoassay for microcystins and Nodularins, Environ. Sci Technol. 2001, vol 35, pp 4849-4856. Then 0.05 mL of anti-microcystin antibody was added to the well. Toxin in the post-release sample was allowed to compete with the microcystin analog for the antibody binding sites for a period of 90 minutes at 20-25° C. Unbound microcystin were then washed away using PBS (phosphate-buffered saline)-Tween wash buffer (10 mM phosphate saline, pH 7.4 with 0.02% Tween). Then 0.1 ml of anti-sheep HRP conjugate was added to each well and incubated for 30 minutes. The conjugate was then washed away using PBS-Tween wash buffer. The enzymes bound to the plates were allowed to react with 0.1 mL of TMB (tetramethylbenzidine) in buffer as a substrate (the TMB in buffer was obtained from BioFx, Owens Mills, Md.) for 20 minutes and 0.05 mL of 2 N sulfuric acid was then added to stop the reaction. Substrate-reaction buffers are also available from other companies. The color was determined at 450 nm using a Molecular Devices VMax Plate Reader. The extent to which color was decreased was a measure of the amount of microcystins in the post-release sample and therefore the sample of lake water. The reaction was calibrated as to a color change using known amounts of Microcystins LR.

The microcystin-specific antibodies used in the ELISA were microcystin-ADDA polyclonal antibodies (Reference: U.S. Pat. No. 6,967,240). The antibodies are reactive with numerous microcystin congeners (Reference: W. J. Fischer et al., Congener-independent Immunoassay for Microcystins and Nodularins, Environ. Sci Technol. 2001, vol 35, pp 4849-4856).

The results of the ELISA analysis for the silver acetate sample are shown in Table 11.

The releasing protocol was also followed using silver nitrate instead of silver acetate (10 ul of a 10 mg/mL silver nitrate solution was added to the sample in the vial). The resulting sample was referred to as the "silver nitrate sample". The results of the ELISA analysis are in Table 11.

TABLE 11

ELISA data - silver acetate or silver sulfate

| Sample | Recovery (ppb) | % of Recovery using Silver sulfate + Tween + Ammonium chloride | % of recovery using Freeze/thaw method |
|---|---|---|---|
| Silver acetate | 1.676 | 48.2 | 38.4 |
| Silver nitrate | 3.856 | 110.8 | 88.4 |

The recoveries for the silver acetate and silver nitrate samples are shown in the second column (from the left) in Table 11. In the third column, that recovery is expressed as a percentage of the control recovery. That control is referred to as the "Silver sulfate+Tween+Ammonium chloride control". In the case of the control, the solutions added into the sample were 100 ul of Reagent A (5 mg/ml silver sulfate in deionized water plus 0.01% Tween-20 in deionized water), the vial was then shaken for 2 minutes followed by another 8 minutes of incubation. Then 10 ul of Reagent B (200 mg/ml ammonium chloride in deionized water) was added to the vial and again the vial was shaken for 2 minutes followed by another 8 minutes of incubation. The results of the ELISA analysis with that control are shown in Table 11.

In the fourth column of Table 11, the recovery is expressed as a percentage of the recovery obtained when the lake sample was frozen then thawed three times in succession. No reagents were present in the vial. That control is referred to as the "Freeze/thaw control". The results of the ELISA analysis with that control are also shown in Table 12.

In another control, the lake water sample was analyzed without any lysis procedure (no additional reagents were added and the sample was not frozen and/or thawed). That control is referred to as the "non-lysed control". The results of the ELISA analysis with that control are also shown in Table 12.

In a further control, the releasing protocol was followed except the reagents in the vial were 100 ul of Reagent A; i.e., silver sulfate and Tween-20. That fourth control is referred to as the "Silver Sulfate+Tween control". The results of the ELISA analysis with that control are also shown in Table 12.

TABLE 12

ELISA data - control samples

| Sample | Recovery (ppb) | % of recovery using Freeze/thaw method |
|---|---|---|
| Freeze/thaw control | 4.36 | 100 |
| Non-lysed control | 0.648 | 14.9 |
| Silver Sulfate + Tween control | 3.415 | 78.3 |
| Silver Sulfate + Tween + ammonium chloride control | 3.480 | 79.8 |

The results in Table 11 (taking into account the results in Table 12) show that silver nitrate is as effective as silver sulfate as a lytic agent, possibly somewhat more so, and significantly better than having no lytic agent present. Silver acetate is less effective than silver sulfate but still causes lysis.

The releasing protocol was also followed using a combination of silver acetate, silver sulfate, and Tween. This was accomplished by adding 100 ul of Reagent A to the sample in addition to 10 ul of a 5 mg/mL silver acetate solution. The resulting sample was referred to as the "silver acetate+silver sulfate+Tween" sample. The result of the ELISA analysis are in Table 13. That procedure was also followed using silver nitrate instead of silver acetate. The resulting sample was referred to as the "silver nitrate+silver sulfate+Tween" sample. The result of the ELISA analysis are also shown in Table 13.

TABLE 13

ELISA data - Combinations of silver sulfate and Tween with either silver acetate or silver nitrate

| Sample | Recovery (ppb) | % of Recovery using Silver sulfate + Tween + Ammonium chloride | % of recovery using Freeze/thaw method |
|---|---|---|---|
| Silver acetate + silver sulfate + Tween | 3.553 | 102 | 81.5 |
| Silver nitrate + silver sulfate + Tween | 3.988 | 114.6 | 91.5 |

The results in Table 13 show that a combination of silver acetate, silver sulfate, and Tween was about as effective as a combination of silver sulfate and Tween (See Table 12) and more effective than silver acetate alone (See Table 11). The results in Table 13 show that a combination of silver nitrate, silver sulfate, and Tween was about as effective as, and possibly even somewhat more effective than, silver sulfate plus Tween (See Table 12) and more effective than silver nitrate alone (See Table 11).

The releasing protocol was also followed using a combination of silver acetate and ammonium chloride. This was accomplished by adding 10 ul of a 5 mg/mL silver acetate solution to the lake water sample and then shaking the vial for 2 minutes followed by an 8 minute incubation, then adding 10 ul of Reagent B to the sample and again shaking the vial for 2 minutes followed by an additional 8 minute incubation. The resulting sample was referred to as the "silver acetate+ammonium chloride sample". The result of the ELISA analysis are in Table 14. The same procedure was followed using silver nitrate instead of silver acetate. The resulting sample was referred to as the "silver nitrate+ammonium chloride" sample. The result of the ELISA analysis are in Table 14.

TABLE 14

ELISA data - Combinations of ammonium chloride plus either silver acetate or silver nitrate

| Sample | Recovery (ppb) | % of Recovery using Silver sulfate + Tween + Ammonium chloride | % of recovery using Freeze/thaw method |
|---|---|---|---|
| Silver acetate + ammonium chloride | 1.827 | 52.5 | 41.9 |
| Silver nitrate + ammonium chloride | 3.545 | 101.9 | 81.3 |

The results in Table 14, in view of the results in Table 11, show that ammonium chloride had little or no effect on the lytic efficiency of silver acetate or silver nitrate, consistent with the observation that it is not necessary to add ammonium chloride to some releasing agents for some samples, but nevertheless it is useful in increasing lysis when in combination with other releasing agents for those samples.

The releasing protocol was also followed using a combination of silver acetate, silver sulfate and Tween plus ammonium chloride. This was accomplished by adding 100 ul of Reagent A to a sample in addition to 10 ul of a 5 mg/mL silver acetate solution and, after shaking for 2 minutes and a further 8 minute incubation, adding 10 ul of Reagent B into the vial, followed by again shaking for 2 minutes and a further 8 minute incubation. The resulting sample was referred to as the "silver acetate+silver sulfate+Tween+ammonium chloride sample". The results of the ELISA analysis are in Table 15. That procedure was also followed using silver nitrate instead of silver acetate. The resulting sample was referred to as the "silver nitrate+silver sulfate+Tween+ammonium chloride sample". The result of the ELISA analysis are also in Table 15.

TABLE 15

ELISA data - Combinations of silver sulfate plus Tween plus ammonium chloride plus either silver acetate or silver nitrate

| Sample | Recovery (ppb) | % of Recovery using Silver sulfate + Tween + Ammonium chloride | % of recovery using Freeze/thaw method |
|---|---|---|---|
| Silver acetate + silver sulfate + Tween + ammonium chloride | 3.429 | 98.5 | 78.6 |

TABLE 15-continued

ELISA data - Combinations of silver sulfate plus Tween plus ammonium chloride plus either silver acetate or silver nitrate

| Sample | Recovery (ppb) | % of Recovery using Silver sulfate + Tween + Ammonium chloride | % of recovery using Freeze/thaw method |
|---|---|---|---|
| Silver nitrate + Silver Sulfate + Tween + ammonium chloride | 3.453 | 99.2 | 79.2 |

The results in Table 15 show that the addition of ammonium chloride to a mixture already containing silver acetate, silver sulfate, and Tween was no more effective than that mixture alone. The results in Table 15 also show that the addition of ammonium chloride to a mixture already containing silver nitrate, silver sulfate, and Tween was no more effective than that mixture alone. The results are consistent with the observation that ammonium chloride is not needed in some cases, but nevertheless useful for the lysis of some lake samples.

Example 8

Silver Nitrate with Another Lake Sample

A lake sample, different from that analyzed in any of the foregoing Examples, was treated using the releasing protocol specified in Example 7, with the following releasing agent preparations:
1) Silver nitrate (10 ul);
2) Silver nitrate (10 ul)+100 ul Reagent A (silver sulfate+Tween);
3) Silver nitrate (10 ul) followed by 10 ul Reagent B (ammonium chloride);
4) Silver nitrate (10 ul)+100 ul Reagent A (silver sulfate+Tween) followed by 10 ul Reagent B (ammonium chloride);
5) As a control, 100 ul Reagent A (Silver sulfate+Tween) followed by 10 ul Reagent B (ammonium chloride)

Samples treated with releasing agent preparations 1 and 2 were shaken for 2 minutes followed by 8 minutes further incubation. Samples treated with releasing agent preparations 3, 4 and 5, prior to the addition of Reagent B, were shaken for 2 minutes followed by 8 minutes further incubation and, after the addition of Reagent B, were again shaken for 2 minutes followed by 8 minutes further incubation. The results are shown in Table 16.

TABLE 16

ELISA data - silver nitrate alone and in combinations

| Sample | Recovery (ppb) | % of Recovery using Silver sulfate + Tween + Ammonium chloride |
|---|---|---|
| Silver nitrate | 56.6 | 30.0 |
| Silver nitrate + silver sulfate + Tween | 135.2 | 71.6 |
| Silver nitrate + ammonium chloride | 50.1 | 26.5 |
| Silver nitrate + silver sulfate + Tween + ammonium chloride | 209.8 | 111.1 |
| Control: silver sulfate + Tween + ammonium chloride | 188.8 | 100 |

The results show that, in this case, addition of silver nitrate, silver sulfate, and Tween provided superior recovery compared to silver nitrate alone.

Example 9

Silver Nitrate with Additional Lake Samples

The procedure described in Example 7 using a combination of silver nitrate, silver sulfate and Tween followed by ammonium chloride was applied to four additional lake samples, Samples 1 through 4, which were not analyzed in any of the foregoing Examples. As a control, the procedure described in Example 7 for silver sulfate and Tween plus ammonium chloride was followed for each sample.

The results are shown in Table 17.

TABLE 17

Analysis of four additional lake samples

| Sample | Control: Silver Sulfate + Tween + Ammonium chloride (Recovery in ppb) | Silver Nitrate + Silver Sulfate + Tween + Ammonium chloride (Recovery in ppb) | % of recovery with control |
|---|---|---|---|
| Sample 1 | 4.71 | 5.39 | 114.4 |
| Sample 2 | 3.24 | 3.32 | 102.5 |
| Sample 3 | 3.125 | 3.227 | 103.3 |
| Sample 4 | 416.2 | 378.9 | 91.0 |

The results show that, over a hundred-fold range of microcystin concentrations, recoveries of microcystins were about the same, regardless of whether or not silver nitrate was used in addition to silver sulfate, Tween, and ammonium chloride, illustrating further that for certain lake samples, silver sulfate plus Tween plus ammonium chloride without additional silver nitrate provided adequate lysis.

Example 10

Use of Higher Concentrations of Silver Nitrate with Additional Lake Samples

Lake samples 1, 2 and 4 of Example 9 were also tested following the releasing protocol of Example 7 (and Example 9) specified for silver nitrate plus silver sulfate and Tween (i.e., 10 ul silver nitrate and 100 ul Reagent A), followed by incubation with ammonium chloride (i.e., 10 ul Reagent B), except that 50 ul of silver nitrate solution was added instead of 10 ul, making the final reaction concentration about 5 times that used in Examples 7 and 9. The analysis was done 3 days after that in Example 9. During that 3-day period, the samples were stored refrigerated. The results using 50 ul of silver nitrate solution are shown in Table 18, with the control data in the left hand column being that also used in the left hand column of Table 17 (See Example 9).

TABLE 18

Analysis of four additional lake samples

| Sample | Control: Silver Sulfate + Tween + Ammonium chloride (Recovery in ppb) | Silver Nitrate (5x) + Silver Sulfate + Tween + Ammonium chloride (Recovery in ppb) | % of recovery with control |
|---|---|---|---|
| Sample 1 | 4.71 | 4.994 | 106.0 |
| Sample 2 | 3.24 | 2.558 | 79.0 |
| Sample 4 | 416.2 | 372.00 | 89.4 |

The results in Table 18, in view of the results in Table 17, show that, over a 100-fold range of microcystin concentrations, increasing the concentration of silver nitrate about 5-fold (when in combination with approximately the same concentrations of silver sulfate, Tween and ammonium chloride utilized in Examples 9) does not increase lysis and subsequent release of microcystins.

Example 11

Filtration of Samples after Lysis

Lake sample 4 of Example 9 was, with the noted exceptions, also tested following the releasing protocol specified in Example 7 with the following releasing agent preparations:

1) Silver nitrate (50 ul);
2) Silver nitrate (50 ul) plus 100 ul Reagent A (silver sulfate plus Tween), followed by addition of 10 ul of Reagent B (ammonium chloride);
3) Silver nitrate (50 ul) plus 100 ul Reagent A (silver sulfate plus Tween), followed by addition of 20 ul of Reagent B (ammonium chloride); and
4) As a control, 100 ul Reagent A (silver sulfate plus Tween) followed by addition of 10 ul of Reagent B (ammonium chloride).

Samples treated with releasing preparation (1) were shaken for 2 minutes followed by 8 minutes further incubation. Samples treated with releasing preparations (2), (3) and (4), prior to the addition of Reagent B, were shaken for 2 minutes followed by 8 minutes further incubation and, after the addition of Reagent B, were again shaken for 2 minutes followed by 8 minutes further incubation.

At the end of the releasing protocol, but before the ELISA analysis was done, the lysed samples were filtered with glass fiber filters, each corresponding to a small circular piece punched out of a glass fiber sheet obtained from Ahlstrom Filtration LLC, Bethune, S.C., and then inserted into a 1 ml pipette tip (from VWR). The analysis was done 4 days after that in Example 9, during which time the samples were stored refrigerated. The results are shown in Table 19.

TABLE 19

Effect of filtering lysed lake samples

| Sample | Recovery (in ppb) | % of recovery with control |
|---|---|---|
| 1) Silver nitrate (5×) | 32.76 | 8.8 |
| 2) Silver nitrate (5×) + silver sulfate + Tween + Ammonium chloride | 387.4 | 103.6 |
| 3) Silver nitrate (5×) + silver sulfate + Tween + 2 × Ammonium chloride | 422.4 | 112.9 |
| 4) Control: silver sulfate + Tween + Ammonium chloride | 374.1 | 100.0 |

The results in Table 19 confirm those in Table 16: Recovery is improved using silver sulfate and Tween and ammonium chloride in addition to silver nitrate. It can be seen that increasing the concentration of the ammonium chloride increased the recovery slightly. The results also show that filtration after lysis does not interfere with lytic recovery of microcystins.

Example 12

Silver Bromate, Silver Sulfate, Silver Trifluoroacetate, and Silver (I) Fluoride Lake sample 2 of Example 9 was tested (20 days after the tests performed for Example 9) in several different ways. In one instance, the procedure of Example 7 was followed as specified for silver acetate (without additional silver sulfate, Tween or ammonium chloride) except that instead of 10 ul of a 5 mg/mL silver acetate solution, the following were used:

1) 100 ul of a 1 mg/ml silver bromate in deionized water solution;
2) 10 ul of a 10 mg/ml silver perchlorate in deionized water solution;
3) 10 ul of a 10 mg/ml silver trifluoroacetate in deionized water solution; or
4) 100 ul of a 1 mg/ml silver (I) fluoride in deionized water solution;

As a control, the lake sample was treated, as in Example 7, with silver sulfate plus Tween followed by ammonium chloride. The Recovery of microcystins for the control was 1.591 ppb.

The results are shown in Table 20.

TABLE 20

Additional silver salts

| Reagent | Recovery (in ppb) | % of recovery with silver sulfate + Tween + ammonium choride |
|---|---|---|
| Silver bromate | 0.937 | 58.9 |
| Silver perchlorate | 1.118 | 70.3 |
| Silver trifluoroacetate | 0.954 | 60.0 |
| Silver (I) fluoride | 1.326 | 83.3 |

The results show that all four salts were effective lysing agents.

All four salts were again tested except that also present was silver sulfate plus Tween in the amounts used in Example 7. The results are shown in Table 21.

TABLE 21

Additional silver salts - in combination with silver sulfate plus Tween

| Reagent in addition to silver sulfate + Tween | Recovery (in ppb) | % of recovery with silver sulfate + Tween + mmonium choride |
|---|---|---|
| Silver bromate | 1.179 | 74.1 |
| Silver perchlorate | 1.233 | 77.5 |
| Silver trifluoroacetate | 1.208 | 75.9 |
| Silver (I) fluoride | 1.158 | 72.8 |

The results in Table 21, in view of the results in Table 20, show a slight increase in microcystin recoveries using silver sulfate plus Tween in addition to either silver bromate, silver perchlorate, or silver trifloroacetate, compared to the respective recoveries obtained with those three silver salts alone.

All four salts were again tested except that also present was ammonium chloride in the amounts and sequence used in Example 7. The results are shown in Table 22.

TABLE 22

Additional silver salts - in combination with ammonium chloride

| Reagent in addition to ammonium chloride | Recovery (in ppb) | % of recovery with silver sulfate + Tween + ammonium choride |
|---|---|---|
| Silver bromate | 1.001 | 62.9 |
| Silver perchlorate | 1.314 | 82.6 |
| Silver trifluoroacetate | 1.017 | 63.9 |
| Silver (I) fluoride | 1.504 | 94.5 |

The results in Table 22, in view of the results in Table 20, show a slight increase in microcystin recoveries using ammonium chloride in addition to silver bromate, silver perchlorate, silver trifloroacetate, or silver (I) fluoride, compared to the respective recoveries obtained with those four silver salts alone.

All four salts were again tested except that also present was silver sulfate and Tween, followed by ammonium chloride, in the amounts used in Example 7. The results are shown in Table 23.

TABLE 23

Additional silver salts - in combination with ammonium chloride

| Reagent in addition to silver sulfate + Tween and ammonium chloride | Recovery (in ppb) | % of recovery with silver sulfate + Tween + ammonium choride |
|---|---|---|
| Silver bromate | 1.592 | 100.1 |
| Silver perchlorate | 1.757 | 110.4 |

TABLE 23-continued

Additional silver salts - in combination with ammonium chloride

| Reagent in addition to silver sulfate + Tween and ammonium chloride | Recovery (in ppb) | % of recovery with silver sulfate + Tween + ammonium choride |
|---|---|---|
| Silver trifluoroacetate | 1.618 | 101.7 |
| Silver (I) fluoride | 1.522 | 95.7 |

The results in Table 23, in view of the results in Tables 20, 21 and 22, show an increase in microcystin recoveries using silver sulfate, Tween and ammonium chloride, in the manner specified, in addition to silver bromate, silver perchlorate, silver trifloroacetate, or silver (I) fluoride, compared either (1) to the respective recoveries obtained with those four silver salts alone or (2) to those salts either with silver sulfate plus Tween or (3) those salts with ammonium chloride.

What is claimed is:

1. A method of releasing a cyanobacterial toxin in a suspension comprising cyanobacteria suspended in an aqueous medium, wherein said method comprises adding a releasing agent to an aliquot of the suspension so as to release toxins from the bacteria into the medium, wherein the releasing agent is a metal salt that comprises a manganese atom and which can dissociate in water to release the manganese atom as a manganese ion.

2. A method of claim 1 further comprising the step of adding Tween and ammonium chloride to the aliquot of the suspension.

3. A method of claim 1 wherein the toxin is selected from the group consisting of microcystins, nodularins, anatoxin-α, anatoxin-a(S), aplysiatoxins, cylindrospermopsins, lyngbyatoxin-a, and saxitoxins.

4. A method of claim 3 wherein the toxin is a selected from the group consisting of a microcystin and a nodularin.

5. A method of claim 4 wherein the toxin is a microcystin.

* * * * *